(12) United States Patent
Kikuchi et al.

(10) Patent No.: US 8,148,213 B2
(45) Date of Patent: Apr. 3, 2012

(54) METHOD OF PRODUCING A BIOSENSOR

(75) Inventors: Hiroaki Kikuchi, Chitose (JP);
Tomoaki Yamabayashi, Chitose (JP);
Osamu Takahashi, Chitose (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 0 days.

(21) Appl. No.: 13/028,684

(22) Filed: Feb. 16, 2011

(65) Prior Publication Data
US 2011/0212562 A1 Sep. 1, 2011

(30) Foreign Application Priority Data

Feb. 17, 2010 (JP) ................................ 2010-032625

(51) Int. Cl.
*H01L 21/00* (2006.01)
*H01L 21/8232* (2006.01)
*H01L 21/335* (2006.01)
*H01L 21/84* (2006.01)

(52) U.S. Cl. .......... 438/142; 438/49; 438/149; 438/153; 438/154; 257/E21.051; 257/E21.4; 257/E21.37

(58) Field of Classification Search ........... 257/E21.051, 257/E21.4, E21.41, E21.37
See application file for complete search history.

(56) References Cited

U.S. PATENT DOCUMENTS

| 7,829,362 B2* | 11/2010 | Fukutani et al. ................ 438/49 |
| 2008/0063566 A1* | 3/2008 | Matsumoto et al. ......... 422/68.1 |
| 2011/0042673 A1* | 2/2011 | Yamabayashi et al. ......... 257/53 |
| 2011/0291075 A1* | 12/2011 | Subagyo et al. ................ 257/29 |
| 2011/0291673 A1* | 12/2011 | Shibata et al. ................ 324/649 |

FOREIGN PATENT DOCUMENTS

| JP | 2004-085392 A | 3/2004 |
| JP | 2006-201178 A | 8/2006 |
| JP | 2007-139762 A | 6/2007 |

\* cited by examiner

*Primary Examiner* — Mohsen Ahmadi
(74) *Attorney, Agent, or Firm* — Washida & Associates

(57) ABSTRACT

A method for manufacturing a biosensor includes forming a laminate of a first silicon oxide film and a polysilicon film on one surface of a silicon substrate; forming a second silicon oxide film on the other surface of the silicon substrate; forming a source electrode, a drain electrode, and a channel on the first silicon oxide film, the channel connecting the source electrode and the drain electrode; and removing the polysilicon film.

4 Claims, 5 Drawing Sheets

METHOD OF PRODUCING A BIOSENSOR

CROSS REFERENCE TO RELATED APPLICATION

This application is entitled and claims the benefit of Japanese Patent Application No. 2010-32625 filed on Feb. 17, 2010, the disclosure of which including the specification, drawings and abstract is incorporated herein by reference in its entirety.

TECHNICAL FIELD

This disclosure relates to a manufacturing method of a biosensor having a field effect transistor.

BACKGROUND ART

Biosensors that utilize a field effect transistor have heretofore been proposed (see Patent Literatures 1 to 3). Generally, in such a field-effect transistor biosensor, source/drain electrodes and a channel are formed on an insulating film formed on a semiconductor substrate, and in many cases, a reaction field is disposed on the channel or insulating film on the semiconductor substrate. Target recognition molecules are often immobilized on the reaction field.

The target recognition molecules immobilized on the reaction field are allowed to recognize a target substance. A source-drain current upon target recognition is measured to determine the presence or concentration of the target substance supplied to the reaction field.

CITATION LIST

Patent Literature

PTL 1: Japanese Patent Application Laid-Open No. 2004-85392
PTL 2: Japanese Patent Application Laid-Open No. 2006-201178
PTL 3: Japanese Patent Application Laid-Open No. 2007-139762

SUMMARY OF INVENTION

Technical Problem

In the conventional manufacturing method, manufactured field-effect biosensors, even when manufactured under the same condition, sometimes have significantly different characteristics, a potential cause of yield reduction. The inventors pinned down one of the causes to the generation of defects in the insulating film on the semiconductor substrate at a region where a reaction field is to be disposed during the manufacturing process, particularly during the semiconductor manufacturing process in which a channel and source/drain electrodes are formed. The inventors established that one cause of the generation of defects in the insulating film on the semiconductor substrate is damage to the insulating film due to physical contact to the conveyor line or other member during transfer.

It is therefore an object of the present invention to provide a method for manufacturing a field-effect transistor biosensor in high yield.

Solution to Problem

In the present invention, upon formation of a channel and source/drain electrodes during manufacturing of a field-effect transistor biosensor, a region corresponding to a reaction field is protected with a polysilicon film, avoiding possible damage to the reaction field. Specifically, the present invention relates to manufacturing methods of a biosensor given below.

[1] A method for manufacturing a biosensor including: a silicon substrate; a first silicon oxide film formed on one surface of the silicon substrate; a reaction field formed on the first silicon oxide film; a gate electrode formed on or above the first silicon oxide film; a second silicon oxide film formed on the other surface of the silicon substrate; a source electrode formed on the second silicon oxide film; a drain electrode formed on the second silicon oxide film; and a channel connecting the source electrode and the drain electrode, the channel formed on the second silicon oxide film, the method comprising:

forming a laminate of a first silicon oxide film and a polysilicon film on one surface of a silicon substrate;

forming a second silicon oxide film on the other surface of the silicon substrate;

forming a source electrode, a drain electrode, and a channel on the second silicon oxide film, the channel connecting the source electrode and the drain electrode;

removing the polysilicon film; and disposing a gate electrode on or above the one surface of the silicon substrate.

[2] The manufacturing method according to [1], wherein the polysilicon film is 1,000 Å or more in thickness.

[3] The manufacturing method according to [1], wherein the first silicon oxide film is 1,000 Å or more in thickness.

[4] The manufacturing method according to [1], wherein a target recognition molecule is immobilized on the reaction field.

Advantageous Effects of Invention

With the present invention, field-effect transistor biosensors can be manufactured in high yield.

DESCRIPTION OF EMBODIMENTS

1. Biosensor

A biosensor according to the present invention includes a silicon substrate, a field effect transistor disposed thereon, and a reaction field.

In the biosensor, a silicon oxide film is deposited on both surfaces of the silicon substrate. On the silicon oxide film formed on one surface of the silicon substrate, a reaction field and a gate electrode are disposed. On the silicon oxide film formed on the other surface of the silicon substrate, a source electrode, a drain electrode, and a channel connecting the source and drain electrodes are disposed.

Typically, target recognition molecules capable of selectively binding to a target substance are bound to the reaction field.

A target detection flow of the biosensor includes the steps of providing a sample that may contain a detection target to a reaction field; allowing the detection target in the sample to react with target recognition molecules immobilized on the reaction field; and measuring a source-drain current while applying a predetermined gate voltage, to identify and quantify the detection target in the sample.

Figure 1:
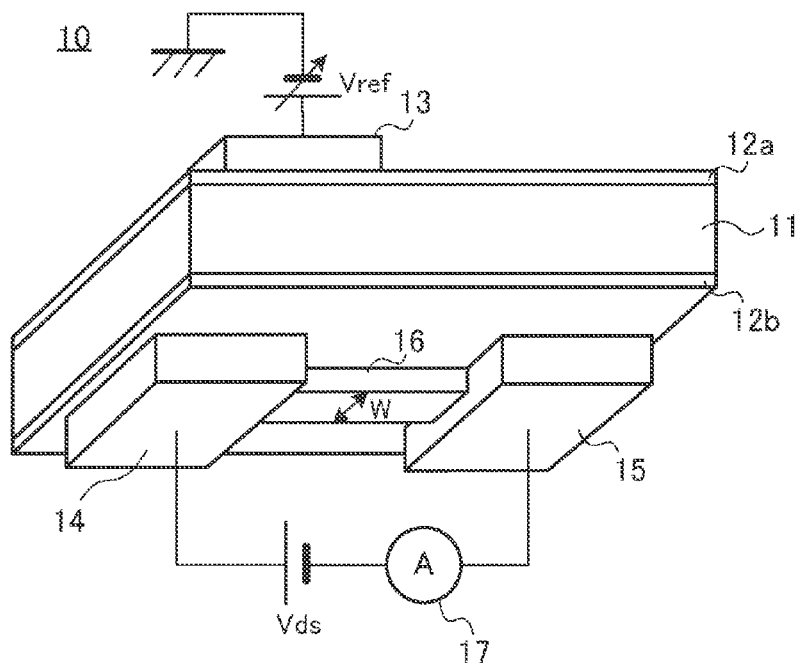
FIG. 1 is a perspective view schematically illustrating a configuration of a biosensor according to the present invention.
Figure 2:
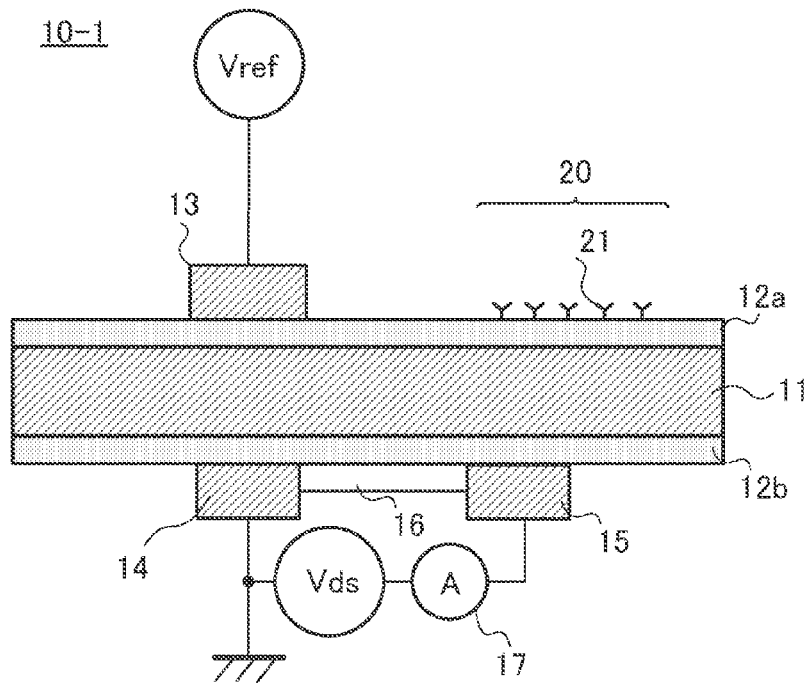
FIG. 2 is a sectional view schematically illustrating a configuration of a first example of a biosensor according to the present invention.
Figure 3:
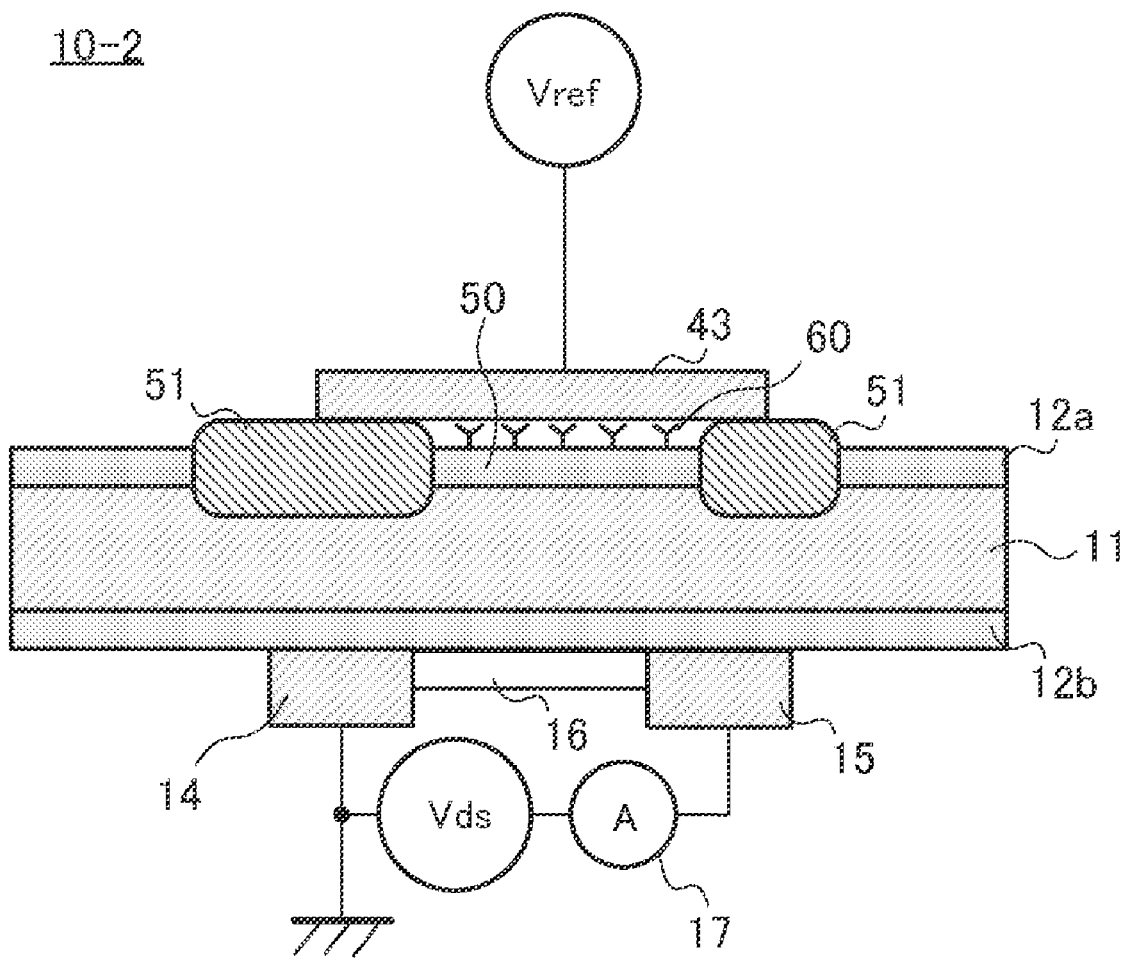
FIG. 3 is a sectional view schematically illustrating a configuration of a second example of a biosensor according to the present invention.

FIG. 1 is a perspective view schematically illustrating a configuration of biosensor 10 according to the present invention. FIG. 2 is a sectional view schematically illustrating a configuration of biosensor 10-1 according to Embodiment 1 of the present invention. FIG. 3 is a sectional view schematically illustrating a configuration of biosensor 10-2 according to Embodiment 2 of the present invention.

As illustrated in FIG. 1, in biosensor 10, silicon oxide films 12a and 12b, which are insulating films, are formed on both surfaces of silicon substrate 11, respectively. Gate electrode 13 is formed on or above the surface of silicon substrate 11 on which silicon oxide film 12a is formed. Reference voltage Vref is applied to gate electrode 13. Gate electrode 13, silicon oxide film 12a, and silicon substrate 11 form a metal-insulator-semiconductor (MIS) structure. Therefore, a gate voltage is not applied directly to silicon substrate 11. The material of gate electrode 13 is not particularly limited, as long as it is electrically conductive, and may be, for example, a metal such as gold, platinum, titanium or aluminum, or a conductive plastic.

Drain electrode 14 and source electrode 15 are formed on the surface of silicon substrate 11 on which silicon oxide film 12b is formed. Drain electrode 14 and source electrode 15 are electrically connected via channel 16 on silicon oxide film 12b.

Channel 16 is preferably formed of polysilicon. As a result, silicon oxide film 12b, drain electrode 14, source electrode 15, and channel 16 form a typical thin film transistor (TFT) structure, and therefore silicon oxide film 12b, drain electrode 14, source electrode 15, and channel 16 can be formed through a semiconductor manufacturing process similar to those used for TFT manufacture.

Since channel 16 is formed of polysilicon, width W of channel 16 can be selected easily in a semiconductor manufacturing process.

Between drain electrode 14 and source electrode 15, power supply Vds and ammeter 17 are connected via external wiring. By this means, a predetermined voltage is applied between drain electrode 14 and source electrode 15 by power supply Vds, and a current that flows across channel 16 is measured by ammeter 17.

The distance between drain electrode 14 and source electrode 15 is not particularly limited, but is normally on the order of 0.5 to 10 μm. This distance may be further reduced in order to facilitate connection of the electrodes by channel 16. The shape and size of the source and drain electrodes are not particularly limited, and can be determined as appropriate depending on the intended purpose.

Biosensor 10-1 illustrated in FIG. 2 includes reaction field 20 on the surface of the substrate on which silicon oxide film 12a is formed. Reaction field 20 means an area in which a measurement sample (typically solution) is to be provided. Target recognition molecules 21 are immobilized on reaction field 20. Examples of target recognition molecules include proteins such as antibodies, enzymes and lectin, nucleic acid, oligosaccharides or polysaccharides, and substances having the structure of the foregoing. Immobilizing target recognition molecules on the reaction field allows for specific detection of specific types of proteins or chemicals.

Reaction field 20 and gate electrode 13 are preferably disposed on the same silicon oxide film, i.e., either silicon oxide film 12a or 12b, most preferably disposed on the silicon oxide film not provided with drain electrode 14 and source electrode 15 (silicon oxide film 12a in FIG. 2). It is also preferable that reaction field 20 and gate electrode 13 be formed as close as possible to each other on the same silicon oxide film 12a. For example, gate electrode 13 may be disposed above or around reaction field 20. With this configuration, voltage changes in channel 16 in response to concentration changes of a detection target provided in reaction field 20 can be made larger, so that measurement sensitivity can be increased.

In FIG. 2, although silicon oxide film 12a provided with reaction field 20 is uniform over the entire surface, a region provided with reaction field 20 may be thinner than the surrounding silicon oxide film 12a. More specifically, reaction field 20 is preferably formed inside a concave. This not only allows a sample solution to be efficiently retained in reaction field 20, but also allows the lines of electric force leaking out in substrate surface direction from gate electrode 13 to more efficiently pass through reaction field 20. Alternatively, a barrier wall surrounding reaction field 20 may be provided on silicon oxide film 12a for efficient retaining of sample solution in reaction field 20.

Biosensor 10-2 illustrated in FIG. 3 has a reaction field provided inside a concave. In FIG. 3, constituent parts identical to those in FIG. 2 are assigned the same reference signs as in FIG. 2, and duplicate descriptions thereof are not given.

As illustrated in FIG. 3, reaction field (gate oxide film) 50 facing gate electrode 43, and barrier section 51 surrounding reaction field 50, are formed on the surface of silicon substrate 11 on which silicon oxide film 12a is formed. Reaction field 50 immobilizes thereon target recognition molecules 60. In this embodiment, reaction field 50 and barrier section 51 are both made of silicon oxide.

The thickness of reaction field 50 is assumed to be 200 nm or less, and in practice, it is preferably on the order of 1 to 200 nm (e.g., 100 nm). The thickness of barrier section 51 is assumed to be greater than that of reaction field 50 as well as be not greater than several thousands of nanometers, and in practice, it is preferably be on the order of 200 to 1,000 nm (e.g., 600 nm). Furthermore, it is preferable that the difference (i.e., difference in level) between the upper surface of reaction field 50 and the upper surface of barrier section 51 be on the order of 200 to 800 nm (for example, 500 nm). In practice, the area of reaction field 50 is on the order of 25 $mm^2$.

Barrier section 51 preferably, but not necessarily, surrounds the entire reaction field 50. The point is that it is only necessary that barrier section 51 surrounds reaction field 50 to an extent that effluence of a sample solution from reaction field 50 can be prevented.

Thus, in sensor 10-2 illustrated in FIG. 3, barrier section 51 surrounding reaction field 50 blocks a target substance and a target recognition molecule, both fed inside reaction field 50, from spreading beyond the area of reaction field 50. That is, the area over which a sample solution spreads on reaction field 50 can be fixed.

The biosensor according to the present invention can be manufactured in high yield as the silicon oxide film to be provided with a reaction field (i.e., silicon oxide film formed on the surface of the substrate opposite to the surface provided with a channel) is less susceptible to damage during a manufacturing process. In addition to this, the biosensor may offer stable detection sensitivity.

2. Manufacturing Method of Biosensor

A manufacturing method of the present invention includes the steps of: forming a laminate of a silicon oxide film and a polysilicon film on one surface of a silicon substrate (first step); forming a silicon oxide film on the other surface of the silicon substrate (second step); forming a source electrode, a drain electrode, and a channel connecting the source and drain electrodes, on the silicon oxide film formed on the other surface of the silicon substrate (third step); and removing the polysilicon film formed on the one surface of the silicon substrate (fourth step).

Thus, during the third step in which a source electrode, a drain electrode and a channel are formed, the silicon oxide film formed on one surface of the silicon substrate is protected by a polysilicon film. The third step can be carried out using a general semiconductor manufacturing process; for increased work efficiency, this step is preferably carried out with the silicon substrate placed on an automatic conveyor. During transfer, the rear surface of the silicon substrate (surface which is opposite to the surface on which a source electrode, a drain electrode and a channel are to be formed) may be damaged by physical contact to a conveyor member or the like, resulting in low manufacturing yield.

In the manufacturing method of the present invention, by contrast, in the third step, a polysilicon film is deposited on the rear surface of the silicon substrate in addition to a silicon oxide film. Thus, the silicon oxide film on the rear surface of the silicon substrate is less likely to be damaged. By removing the polysilicon film after the third step to expose the silicon oxide film, a silicon oxide film with normal surface is produced. Subsequently, by forming a reaction field thereon, a non-defective biosensor is manufactured.

FIGS. 4A to 4K illustrate a manufacturing process flow of a biosensor according to the present invention. First, in the step illustrated in FIG. 4A, silicon oxide films 12a and 12b are formed on both surfaces of a silicon substrate by means of thermal oxidization, respectively. Each silicon oxide film is preferably 1,000 to 5,000 Å in thickness. When the thickness of the silicon oxide film is less than 1,000 Å, it may result in failure to ensure its function as an insulating film. On the other hand, when the thickness of the silicon oxide film is greater than 5,000 Å, it may result in reduced biosensor sensitivity.

Figure 4A:
FIGS. 4A to 4K illustrate a manufacturing process flow of a biosensor according to the present invention.
Figure 4B:

In the step illustrated in FIG. 4B, polysilicon films 30a and 30b are formed on silicon oxide films 12a and 12b, respectively. The polysilicon films may be deposited by CVD. Polysilicon film 30a is preferably 1,000 to 4,000 Å in thickness. When the thickness of polysilicon film 30a is less than 1,000 Å, it may result in failure to fully prevent possible damage to silicon oxide film 12a caused by physical contact to the conveyor member. The thickness of polysilicon film 30a may be 4,000 Å, but it may lead to high manufacturing costs.

Figure 4C:
Figure 4D:
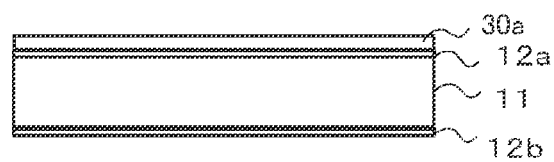

In the step illustrated in FIG. 4C, silicon oxide film 12b and polysilicon film 30b, formed on one side of silicon substrate 11, are removed. In the step illustrated in FIG. 4D, another silicon oxide film 12b is formed on the surface of silicon substrate 11 from which silicon oxide film 12b and polysilicon film 30b have been removed. Formation of silicon oxide film 12b may be accomplished by thermal oxidization, as with the first silicon oxide film 12b. Alternatively, the state as illustrated in FIG. 4D may be accomplished by selectively removing polysilicon film 30b, without removing silicon oxide film 12b in FIG. 4B.

Figure 4E:
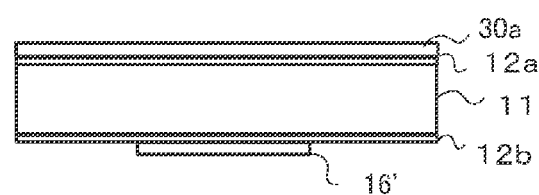

In the step illustrated in FIG. 4E, polysilicon film 16' is formed at a predetermined position (the position where a channel is to be formed) on silicon oxide film 12b. Formation of polysilicon film 16' may be accomplished by depositing amorphous silicon at the predetermined position and irradiating it with a laser beam for polycrystallization.

Figure 4F:
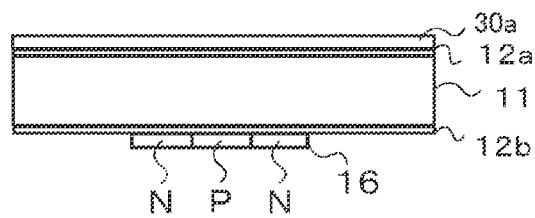

In the step illustrated in FIG. 4F, polysilicon film 16' is doped with an impurity, after which the impurity is diffused throughout the film by heat treatment to form channel 16. Channel 16 may be of NPN-type, PNP-type, NiN-type, or PiP-type. When channel 16 is NPN type or PNP type, the band gap of the channel is large, and therefore, leakage current tend to be small compared to the NiN-type or PiP-type channel. Consequently, with an NPN-type or PNP-type channel, an electric circuit that can reduce current consumption in stand-by mode can be readily constructed. The NiN-type or PiP-type channel, on the other hand, may be manufactured in fewer steps than the NPN-type or PNP-type channel.

Figure 4G:
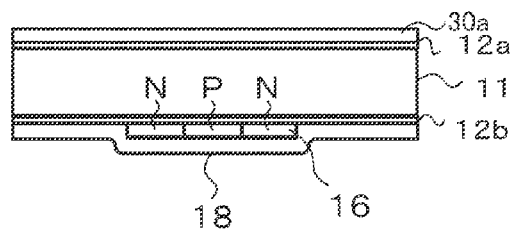
Figure 4H:
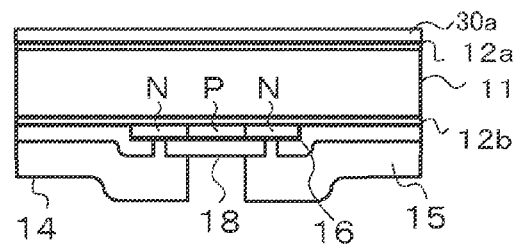

In the step illustrated in FIG. 4G, interlayer insulating film 18 that covers channel 16 is formed. Interlayer insulating film 18 is made of hafnium oxide, for example. In the step illustrated in FIG. 4H, drain electrode 14 and source electrode 15 are formed, which are electrically connected to channel 16 via contact holes.

Figure 4I:
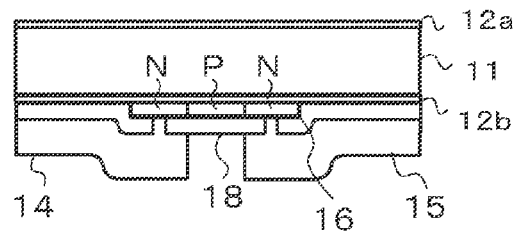

In the step illustrated in FIG. 4I, polysilicon film 30a formed on the other surface of silicon substrate 11 is removed. Removal of polysilicon film 30a may be accomplished by etching with dry etching gas. Examples of dry etching gas include chlorine gas and hydrogen bromide gas. The reason for employing drying etching is that polysilicon film 30a can be selectively removed without removing silicon oxide film 12a.

Figure 4J:
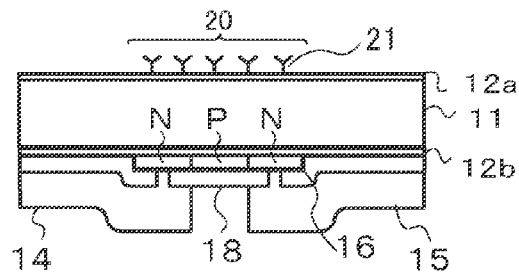

In the step illustrated in FIG. 4J, reaction field 20 is formed on silicon oxide film 12a which has been exposed by removal of polysilicon film 30a. Because generation of defects is suppressed on the exposed silicon oxide film 12a, reaction field 20 is properly created thereon. Target recognition molecules 21 are then immobilized on reaction field 20.

Figure 4K:
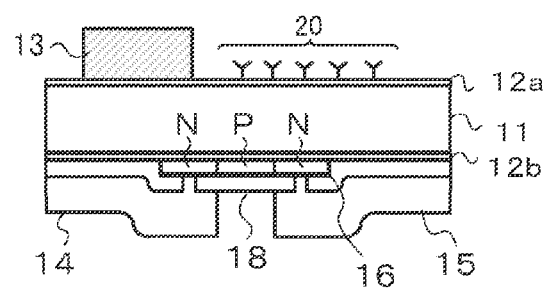

In the step illustrated in FIG. 4K, gate electrode 13 is disposed in the vicinity of reaction field 20. In this way a biosensor according to the present invention is manufactured. It is only necessary that gate electrode 13 be disposed in the vicinity of reaction field 20, but may be disposed so as to surround reaction field 20. The material of gate electrode 13 may be, for example, a metal such as gold, platinum, titanium or aluminum, or a conductive plastic. The gate electrode is disposed on or above silicon oxide film 12a. Thus, a gate voltage is not applied directly to silicon substrate 11.

In some embodiments, a biosensor of the present invention may have reaction field 50 surrounded by barrier section 51, as illustrated in FIG. 3. With reference to FIGS. 5A to 5D, a method of forming a reaction field surrounded by barrier section 51 will be described. Barrier section 51 may be formed by the LOCOS method.

Figure 5A:
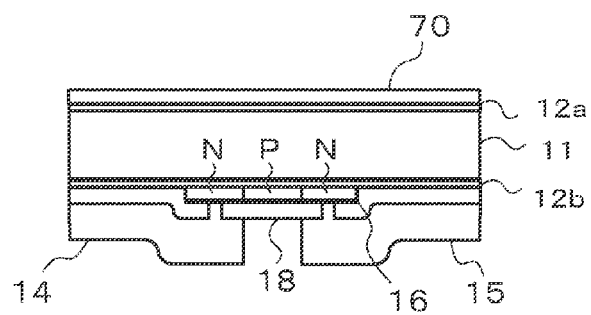
FIGS. 5A to 5E illustrates a process flow in which a reaction field with a barrier section is formed.
Figure 5B:
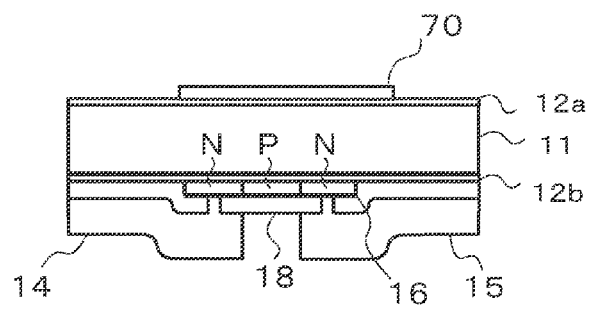

In the step illustrated in FIG. 5A, silicon nitride film 70 is deposited by CVD on silicon oxide film 12a which has been exposed by removal of a polysilicon film (see FIG. 4I). In the step illustrated in FIG. 5B, silicon nitride film 70 is patterned by lithography and etching. A barrier section is formed in a region from which the silicon nitride film has been removed. On the other hand, a reaction field is formed in a region in which the silicon nitride film remains.

Figure 5C:
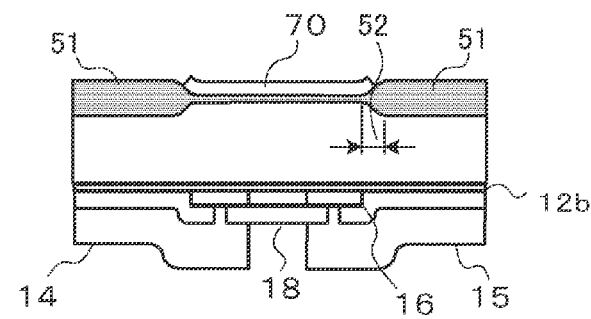

In the step illustrated in FIG. 5C, oxidation treatment is carried out whereby the region from which silicon nitride film 70 has been removed is selectively oxidized. This makes the silicon oxide film thick, forming barrier section 51. On the other hand, the region in which silicon nitride film 70 remains is not oxidized. In this process, the thickly formed silicon oxide film burrows under the silicon nitride film, forming bird's beak 52. Oxidization treatment may be carried out at elevated temperatures (e.g., 1,000° C.) in a wet oxygen atmosphere.

Figure 5D:
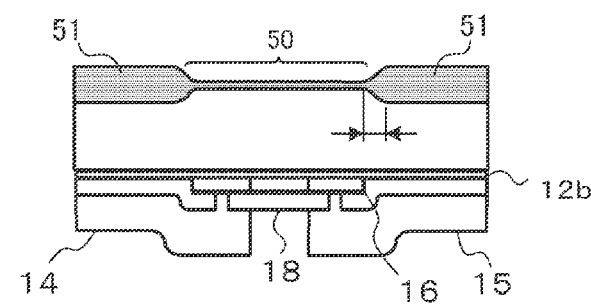
Figure 5E:
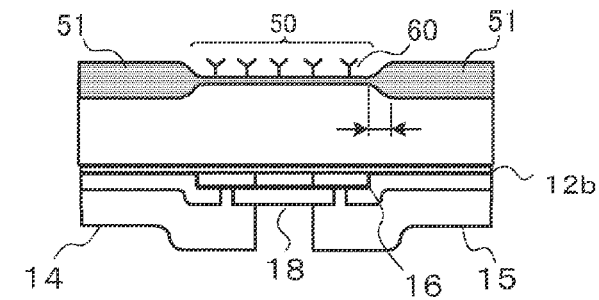

In the step illustrated in FIG. 5D, silicon nitride film 70 is removed, providing a region that serves as reaction field 50. Target recognition molecules 60 are then bound to reaction field 50. Finally, a gate electrode is disposed in the vicinity of reaction field 50. In this way a biosensor according to the present invention is manufactured.

Reference Example 1

A 1350 Å-thick silicon oxide film was formed on both sides of a silicon wafer. A 2,000 Å-thick polysilicon film was then deposited on both sides of the silicon wafer by CVD. The silicon wafer was inverted and transferred by conveyor. The silicon wafer's polysilicon film contacted the conveyor member was removed by etching. Removal was effected by dry etching using chlorine gas.

By vapor deposition, an aluminum film was deposited on the silicon oxide film exposed by removal of the polysilicon film. The aluminum film was patterned using a resist mask—formation of a resin resist film, patterning of the resist film, patterning of an aluminum film, and removal of the resist film—to form 120 aluminum electrodes.

The polysilicon film and silicon oxide film, formed on the surface of the silicon wafer opposite to the surface provided with the aluminum electrodes, were removed by surface grinding to expose the silicon surface. The silicon surface and each of the aluminum electrodes were electrically connected. A voltage sweep from 0V to −40V was applied to each aluminum electrode, and a silicon wafer-to-aluminum electrode current was measured. The number of the devices through which current was not conducted (normal devices), and the number of the devices through which current was conducted (defective devices), were counted.

Reference Example 2

A 1,350 Å-thick silicon oxide film was formed on both sides of a silicon wafer by thermal oxidization. A 3,500 Å-thick polysilicon film was then deposited on both sides of the silicon wafer. As in Reference Example 1, wafer transfer, removal of polysilicon film by etching, formation of 120 aluminum electrodes, exposing of silicon surface by surface grinding, and connecting of silicon surface to aluminum electrodes were then performed.

As in Reference Example 1, a voltage sweep from 0V to −40V was applied to each aluminum electrode, and a silicon wafer-to-aluminum electrode current was measured. The number of the devices through which current was not conducted (normal devices), and the number of the devices through which current was conducted (defective devices), were counted.

Reference Example 3

A 4,000 Å-thick silicon oxide film was formed on both sides of a silicon wafer by thermal oxidization. A 2,000 Å-thick polysilicon film was then deposited on both sides of the silicon wafer. As in Reference Example 1, wafer transfer, removal of polysilicon film by etching, formation of 120 aluminum electrodes, exposing of silicon surface by surface grinding, and connecting of silicon surface to aluminum electrodes were then performed.

As in Reference Example 1, a voltage sweep from 0V to −40V was applied to each aluminum electrode, and a silicon wafer-to-aluminum electrode current was measured. The number of the devices through which current was not conducted (normal devices), and the number of the devices through which current was conducted (defective devices), were counted.

Reference Example 4

A 4,000 Å-thick silicon oxide film was formed on both sides of a silicon wafer by thermal oxidization. A 3,500 Å-thick polysilicon film was then deposited on both sides of the silicon wafer. As in Reference Example 1, wafer transfer, removal of polysilicon film by etching, formation of 120 aluminum electrodes, exposing of silicon surface by surface grinding, and connecting of silicon surface to aluminum electrodes were then performed.

As in Reference Example 1, a voltage sweep from 0V to −40V was applied to each aluminum electrode, and a silicon wafer-to-aluminum electrode current was measured. The number of the devices through which current was not conducted (normal devices), and the number of the devices through which current was conducted (defective devices), were counted.

Comparative Reference Example 1

A 1,350 Å-thick silicon oxide film was formed on both sides of a silicon wafer by thermal oxidization. Wafer transfer was not conducted, thus avoiding physical contact of the silicon oxide film on the rear surface of the silicon wafer to any conveyor member. Thereafter, formation of 120 aluminum electrodes, exposing of silicon surface by surface grinding, and connecting of silicon surface to aluminum electrodes were performed.

As in Reference Example 1, a voltage sweep from 0V to −40V was applied to each aluminum electrode, and a silicon wafer-to-aluminum electrode current was measured. The number of the devices through which current was not conducted (normal devices), and the number of the devices through which current was conducted (defective devices), were counted.

Comparative Reference Example 2

A 1,350 Å-thick silicon oxide film was formed on both sides of a silicon wafer by thermal oxidization. Thereafter, without forming any polysilicon film, wafer transfer, formation of 120 aluminum electrodes, exposing of silicon surface by surface grinding, and connecting of silicon surface to aluminum electrodes were performed as in Reference Example 1.

As in Reference Example 1, a voltage sweep from 0V to −40V was applied to each aluminum electrode, and a silicon wafer-to-aluminum electrode current was measured. The number of the devices through which current was not conducted (normal devices), and the number of the devices through which current was conducted (defective devices), were counted.

Comparative Reference Example 3

A 3,000 Å-thick silicon oxide film was formed on both sides of a silicon wafer by thermal oxidization. Thereafter, without forming any polysilicon film, wafer transfer, formation of 120 aluminum electrodes, exposing of silicon surface by surface grinding, and connecting of silicon surface to aluminum electrodes were performed as in Reference Example 1.

As in Reference Example 1, a voltage sweep from 0V to −40V was applied to each aluminum electrode, and a silicon wafer-to-aluminum electrode current was measured. The number of the devices through which current was not conducted (normal devices), and the number of the devices through which current was conducted (defective devices), were counted.

Defective device counts (out of 120 devices in total) in Reference Examples and Comparative Reference Examples are shown in the following Table 1.

TABLE 1

| | Silicon oxide film thickness | | | |
|---|---|---|---|---|
| | 1,350 Å Without transfer step | 1,350 Å | 3,000 Å | 4,000 Å |
| | | With transfer step | | |
| Poly-silicon film | — | Comparative Reference Example 1 (0/120) | Comparative Reference Example 2 (26/120) | Comparative Reference Example 3 (13/120) |
| 2,000 Å | — | Reference Example 1 (15/120) | — | Reference Example 3 (3/120) |
| 3,500 Å | — | Reference Example 2 (8/120) | — | Reference Example 4 (1/120) |

As seen from Table 1, in the case where a wafer transfer step was not carried out during a device manufacturing process, even when polysilicon films were not used to protect silicon oxide films (see Comparative Reference Example 1), the manufacturing yield was high, with no defective devices produced. However, in the case where a wafer transfer step was carried out during a device manufacturing process, when polysilicon films were not used to protect silicon oxide films (see Comparative Reference Examples 2 and 3), defective devices were produced.

By contrast, in the case where polysilicon films were used to protect silicon oxide films, even when a wafer transfer step was carried out, generation of defective device was suppressed (see Comparative Reference Example 1, and Reference Examples 1 and 2). Moreover, as seen from Table 1, generation of defective device decreased with increasing thickness of the polysilicon film and silicon oxide film (see Reference Examples 1 to 4).

These results suggest that in the case where a biosensor device manufacturing process involves a silicon wafer transfer step, protection of insulating film formed on the silicon wafer surface suppresses the generation of defective device. In particular, protection of a silicon oxide film, an insulating film, by a polysilicon film is preferable because a general semiconductor manufacturing process can be employed and the silicon oxide film can be selectively protected.

INDUSTRIAL APPLICABILITY

According to the present invention, a field-effect transistor biosensor can be manufactured in high yield; therefore, the present invention contributes to the practical use of a field-effect transistor biosensor.

| Reference Signs List | |
|---|---|
| 10, 10-1, 10-2 | Biosensor |
| 11 | Silicon substrate |
| 12a, 12b | Silicon oxide film |
| 13 | Gate electrode |
| 14 | Drain electrode |
| 15 | Source electrode |
| 16 | Channel |
| 16' | Polysilicon film |
| 17 | Ammeter |
| 18 | Interlayer insulating film |
| 20 | Reaction field |
| 21 | Target recognition molecule |
| 30a, 30b | Polysilicon film |
| 43 | Gate electrode |
| 50 | Reaction field |
| 51 | Barrier section |
| 52 | Bird's beak |
| 60 | Target recognition molecule |
| 70 | Silicon nitride film |

The invention claimed is:

1. A method for manufacturing a biosensor including: a silicon substrate; a first silicon oxide film formed on one surface of the silicon substrate; a reaction field formed on the first silicon oxide film; a gate electrode formed on or above the first silicon oxide film; a second silicon oxide film formed on the other surface of the silicon substrate; a source electrode formed on the second silicon oxide film; a drain electrode formed on the second silicon oxide film; and a channel connecting the source electrode and the drain electrode, the channel formed on the second silicon oxide film, the method comprising:
    forming a laminate of a first silicon oxide film and a polysilicon film on one surface of a silicon substrate;
    forming a second silicon oxide film on the other surface of the silicon substrate;
    forming a source electrode, a drain electrode, and a channel on the second silicon oxide film, the channel connecting the source electrode and the drain electrode;
    removing the polysilicon film; and
    disposing a gate electrode on or above the one surface of the silicon substrate.

2. The manufacturing method according to claim 1, wherein the polysilicon film is 1,000 Å or more in thickness.

3. The manufacturing method according to claim 1, wherein the first silicon oxide film is 1,000 Å or more in thickness.

4. The manufacturing method according to claim 1, wherein a target recognition molecule is immobilized on the reaction field.

* * * * *